United States Patent [19]
Nishioka

[11] Patent Number: 5,967,968
[45] Date of Patent: Oct. 19, 1999

[54] APPARATUS AND METHOD FOR DETERMINING THE SIZE OF AN OBJECT DURING ENDOSCOPY

[75] Inventor: Norman S. Nishioka, Wayland, Mass.

[73] Assignee: The General Hospital Corporation, Boston, Mass.

[21] Appl. No.: 09/105,392

[22] Filed: Jun. 25, 1998

[51] Int. Cl.[6] ............................................. A61B 1/00
[52] U.S. Cl. ........................................ 600/117; 600/104
[58] Field of Search .................................. 600/101, 102, 600/103, 104, 117, 118, 167, 168, 176

[56] References Cited

U.S. PATENT DOCUMENTS

| | | | |
|---|---|---|---|
| 1,864,895 | 3/1930 | Vernier | 600/117 |
| 3,817,619 | 6/1972 | Kawahara | 600/117 |
| 3,819,267 | 8/1972 | Kawahara | 600/117 |
| 4,207,594 | 7/1977 | Morris | 358/107 |
| 4,558,691 | 7/1984 | Okada | 600/117 |
| 4,607,622 | 4/1985 | Fritch | 600/117 |
| 4,633,855 | 9/1985 | Baba | 600/117 |
| 4,702,229 | 3/1986 | Zobel | 600/117 |
| 4,825,259 | 2/1988 | Berry | 600/117 |
| 4,980,763 | 6/1989 | Lia | 600/117 |
| 5,239,982 | 11/1992 | Trauthen | 600/117 |
| 5,379,754 | 7/1992 | Tovey | 600/117 |
| 5,445,140 | 6/1993 | Tovey | 600/117 |
| 5,820,547 | 9/1996 | Strobl | 600/117 |

OTHER PUBLICATIONS

Fujino, Endoscopy, "Can Endoscopic Measurement be Made Reliable, Elegant, and Economical? The Search for Computerized Image Processing", 26:486–487, 1994.

Hofstad et al., Endoscopy, "In Situ Measurement of Colorectal Polyps to Compare Video and Fiberoptic Endoscopes", 26:461–465, 1994.

Vakil et al., Gastrointestinal Endoscopy, "Endoscopic Measurement of Lesion Size: Improved Accuracy with Image Processing", 40:178–183, 1994.

Vakil, Endoscopy, "Measurement of Lesions by Endoscopy: An Overview", 27:694–697, 1995.

*Primary Examiner*—John P. Leubecker
*Assistant Examiner*—Ira Hatton
*Attorney, Agent, or Firm*—Fish & Richardson P.C.

[57] ABSTRACT

An endoscopic imaging system for viewing an object within a patient's body cavity includes: an endoscope for viewing an image of the object, the endoscope comprising a distal end, an instrument channel extending therethrough, and a lens at the distal end adjacent the instrument channel; and an elongate probe configured to be inserted through the instrument channel and contact the object, the probe comprising a plurality of unevenly spaced graduations along its length, each graduation indicating a size factor used to scale the image produced by the endoscope. The invention also relates to a method of determining the size of an object in a patient's body cavity including the steps of: generating an image of the object using an instrument; extending a probe having a series of unevenly spaced graduations from the instrument to the object; identifying the graduation on the probe visible in the image nearest to the instrument; and scaling the image viewed by the endoscope by a size factor corresponding to the identified graduation.

24 Claims, 4 Drawing Sheets

APPARATUS AND METHOD FOR DETERMINING THE SIZE OF AN OBJECT DURING ENDOSCOPY

FIELD OF THE INVENTION

The invention relates to endoscopic surgery and an apparatus and method for determining the size of objects during endoscopic surgery.

BACKGROUND OF THE INVENTION

Endoscopes are instruments used to visually examine the interior of a patient during surgery. For example, endoscopes are used to visually examine internal organs such as the colon, bladder, and stomach, the abdominal cavity and peritoneum, joints such as the knee and elbow, and the larynx. Typically, endoscopes are inserted into the patient's body, deliver light to an object being examined, and collect the light reflected from the object. The reflected light carries visual information about the object being examined and can be used to create an image of the object.

Although the image provides useful medical information, it is also important that a surgeon can accurately determine the absolute size of features in the image.

SUMMARY OF THE INVENTION

The invention features a measurement probe for use with an endoscope. The probe allows a surgeon to accurately measure the actual size of features in an image produced by the endoscope. The probe is configured to extend through an instrument channel in the endoscope and contact an object being imaged. Using the probe, a surgeon can measure the distance between the endoscope and an object being imaged. This distance affects the magnification of the object being imaged.

The probe has a series of unevenly spaced graduations. Each graduation on the probe corresponds to a size factor used to scale the size of features in the image produced by the endoscope. Once the probe contacts the object being imaged, the graduation on the probe visible in the image that is nearest the endoscope indicates the appropriate size factor for that image.

In general, in one aspect, the invention features an endoscopic imaging system for viewing an object within a patient's body cavity. The system includes an endoscope for viewing an image of the object, the endoscope including a distal end, an instrument channel extending therethrough, and a lens at the distal end adjacent the instrument channel. The system also includes an elongate probe configured to be inserted through the instrument channel and contact the object, the probe including a plurality of unevenly spaced graduations along its length, each graduation indicating a size factor used to scale the image produced by the endoscope.

Embodiments of the system may include any of the following features.

The graduations on the probe may be spaced such that an image of the object scaled by the size factor corresponding to the graduation nearest the distal end of the endoscope in the image is of a size that is within a constant error of an actual size of the object. For example, the constant error may be about 10 percent. Alternatively, or in addition, the spacing between each pair of adjacent graduations s(N) may be substantially equal to an equation given by $s(N)=w*y^N$ where w and y are constants, and N is the number of graduations between the pair and a distal end of the probe.

The plurality of graduations may be defined by a plurality of bands extending along the length of the probe. At least two of the plurality of bands may each have a different color. In addition, the plurality of bands may each have a different color. Also, the colors of an adjacent pair of bands may indicate a unique graduation.

The endoscope may have an additional instrument channel.

The system may include an analyzer storing the size factors, wherein the analyzer is programmed to receive the image from the endoscope, identify which of the graduations visible in the image is nearest the distal end of the endoscope, and specify the size factor corresponding to the identified graduation. In addition, the system may further include a monitor connected to the analyzer, wherein the monitor displays the image viewed through the endoscope and overlays the image with an electronic measurement grid corresponding to the specified size factor.

Alternatively, the system may include a monitor connected to the endoscope for displaying the image. In addition, the system may include a series of measurement grids configured to overlay the image displayed on the monitor, wherein each measurement grid corresponds to one of the size factors indicated by the graduations of the probe.

In another aspect, the invention features an endoscopic imaging system for viewing an object within a patient's body cavity. The system includes: an endoscope for viewing an image of the object, the endoscope including a distal end and a lens at the distal end; and an elongate probe connected to the endoscope and extendable to contact the object, the probe including a plurality of unevenly spaced graduations along its length, each graduation indicating a size factor used to scale the image viewed through the endoscope.

In a further aspect, the invention features a probe for determining a size of an object viewed through an endoscope. The probe includes: an elongate shaft configured for use with the endoscope and to contact the object; and a plurality of unevenly spaced graduations located along a length of the shaft, each graduation indicating a size factor used to scale the size of the object viewed through the endoscope.

Embodiments of the probe may include any of the following features.

The graduations on the probe may be spaced such that an image of the object scaled by the size factor corresponding to the graduation nearest the distal end of the endoscope in the image is of a size that is within a constant error of an actual size of the object. For example, the constant error may be about 10 percent. Alternatively, or in addition, the spacing between each pair of adjacent graduations s(N) may be substantially equal to an equation given by $s(N)=w*y^N$ where w and y are constants, and N is the number of graduations between the pair and a distal end of the probe.

The plurality of graduations may be defined by a plurality of bands extending along the length of the probe. At least two of the plurality of bands each may have a different color.

Also, the shaft may be configured to be inserted through an instrument channel of the endoscope.

In a further aspect, the invention features a method of determining the size of an object in a patient's body cavity. The method includes: generating an image of the object using an instrument; extending a probe having a series of unevenly spaced graduations from the instrument to the object; identifying the graduation on the probe visible in the image nearest to the instrument; and scaling the image viewed by the endoscope by a size factor corresponding to the identified graduation.

Embodiments of the method may include overlaying the image viewed through the instrument with a measurement grid corresponding to the size factor to scale the image. Also, the optical instrument may be an endoscope.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and not intended to be limiting.

The measurement probe allows a surgeon to accurately determine the size of objects being imaged by an endoscope. In some embodiments, the graduations are spaced such that the size factor indicated by each graduation accurately scales the image to a size that is within a constant fractional error of the actual size of the object being imaged. In many cases, this reduces the number of graduations that are necessary on the probe, e.g., as compared to a ruler with 1 mm graduations. Moreover, for embodiments in which the graduations are formed by a series of colored bands, the graduations can be easily distinguished from one another.

Other features and advantages of the invention will be apparent from the following detailed description, and from the claims.

DETAILED DESCRIPTION

The invention features an endoscopic imaging system in which the size of objects imaged by the system can be accurately and simply determined. The system includes a conventional endoscope and a measurement probe having a series of unevenly spaced graduations. In some embodiments, the graduations on the measurement probe are formed by a series of colored bands, which allows the graduations to be easily distinguished from one another.

Endoscope

Figure 1:
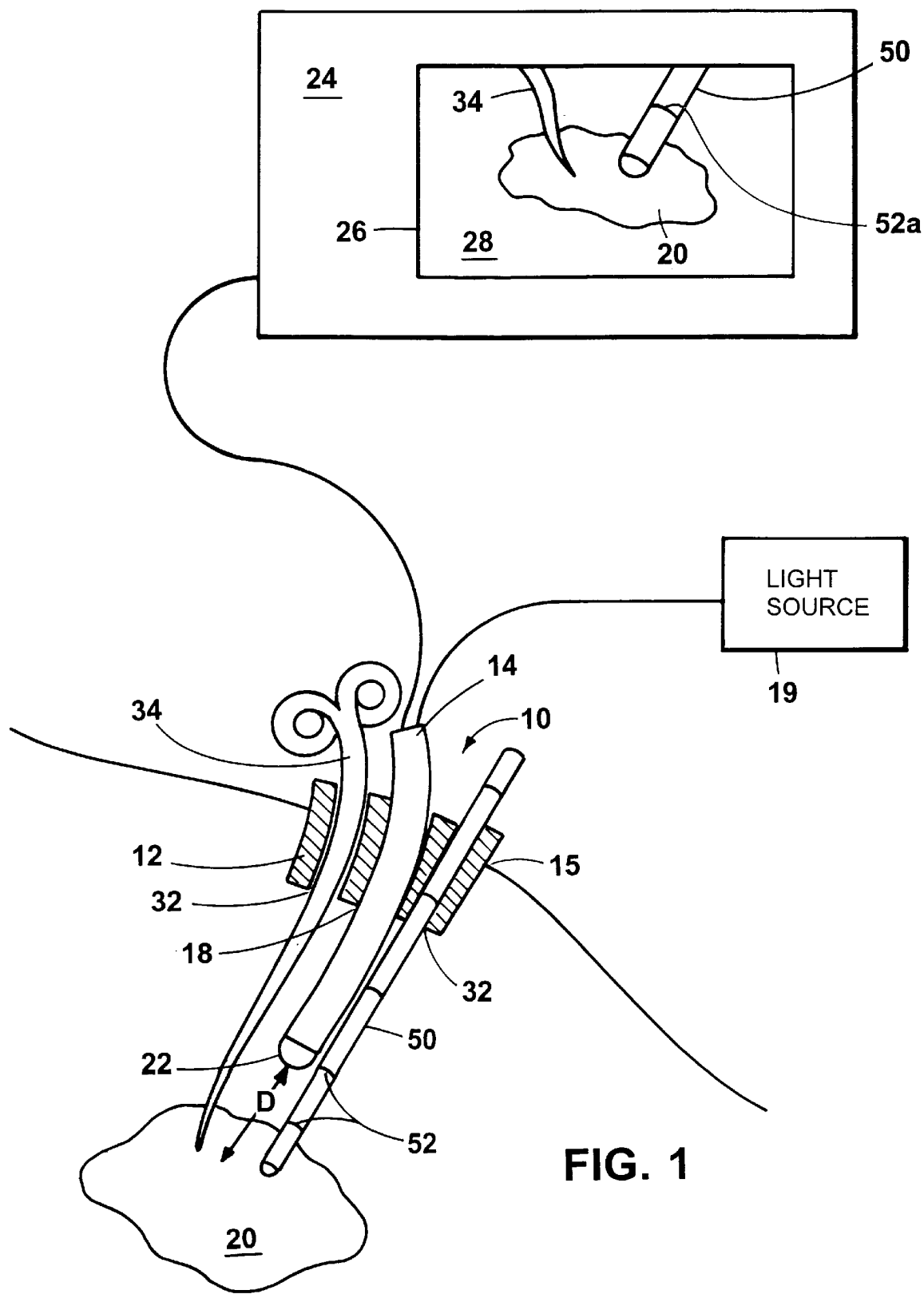
FIG. 1 is a schematic diagram of an endoscopic imaging system that includes a measurement probe for use in determining the size of objects imaged by the system.

FIG. 1 illustrates the use of an endoscope 10 during surgery. Endoscope 10 includes a base 12 and an optical probe 14. Base 12 is secured to an opening 15 into a patient's body cavity 16. Optical probe 14 projects into body cavity 16 through a light delivery channel 18 in base 12. Optical probe 14 delivers light from a light source 19 into body cavity 16 to illuminate an object 20, such as an organ, joint, or lesion. Optical probe 14 also includes a wide angle lens 22 at its distal end for viewing the illuminated object. Lens 22 collects light reflected from object 20 and optical probe 14 directs the collected light to an image processor 24, which includes a monitor 26 for displaying an image 28 of the object.

Using the image displayed on monitor 26 as guidance, a surgeon may manually manipulate object 20. Alternatively, or in addition, the surgeon may manipulate the object using a tool 34, such as a biopsy needle, inserted through an instrument channel 32 in base 12. Also, in other procedures and embodiments, image 28 may be recorded as a photograph, which is subsequently studied.

In any of these cases, the surgeon often requires knowledge of the absolute size of object 20, or other features of image 28. However, the absolute size of a feature in image 28 depends on the magnification M of visual information by endoscope 10. That magnification depends on the distance D between lens 22 and object 20. For example, if the actual size of object 20 is 10 mm, the image produced by the endoscope and displayed on monitor 26 may appear to be 60 mm for a distance D of 10 mm and it may appear to be 40 mm for a distance D of 20 mm. In other words, the magnification M is ×6 for a distance D of 10 mm and ×4 for a distance D of 20 mm. Unfortunately, the distance D may vary during the surgery and from one surgical procedure to another. Moreover, the distance D is not something that a surgeon can readily determine from the image produced by the endoscope. To properly scale the image displayed on the monitor, a measurement probe 50 is inserted through a second instrument channel 34 in base 12.

Measurement Probe

Measurement probe 50 includes a series of unevenly spaced graduations 52 along its length, such as a series of lines or markings. Graduations 52 measure the distance between lens 22 and object 20. In addition, each graduation indicates a size factor used to scale image 28 produced by endoscope 10. By scaling image 28 with the appropriate size factor, the image indicates an absolute size of features therein. As will be described in greater detail further below, graduations 52 are unevenly spaced so that the absolute size in an image scaled by the appropriate size factor is always within a constant fractional error of the actual size.

To determine which graduation indicates the appropriate size factor for a particular image, measurement probe 50 is extended to contact object 20. When probe 50 is so extended, some of its graduations will be visible in the image produced by endoscope 10. The visible graduation closest to lens 22, i.e., graduation 52a, indicates the appropriate size factor for the particular image produced by endoscope 10.

Figure 2A:
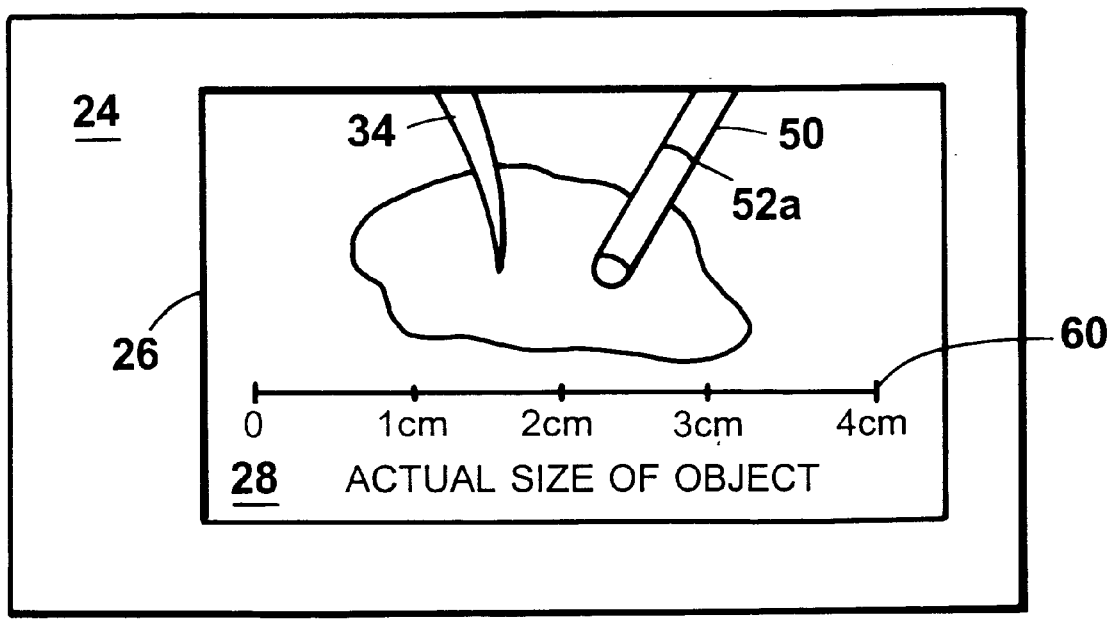
FIGS. 2a and 2b are schematic diagrams of electronic (FIG. 2a) and hardcopy (FIG. 2b) measurement grids, which are used to scale images produced by the endoscopic imaging system in FIG. 1.

In some embodiments, the size factors are stored in image processor 24. Upon receiving the collected light from endoscope 10, image processor 24 constructs the image, identifies which of the visible graduations of measurement probe 50 is closest to lens 22, and recalls the size factor corresponding to that visible graduation. Image processor 24 then displays the image and overlays an electronic measurement grid indicating the absolute dimensions of object 20 displayed in image 28. For example, as shown in FIG. 2a, the electronic measurement grid can be a computer-generated scale 60 visually overlaid on image 28 indicating a grid spacing on the image corresponding to an actual size for the object, e.g., 10 mm.

Figure 2B:
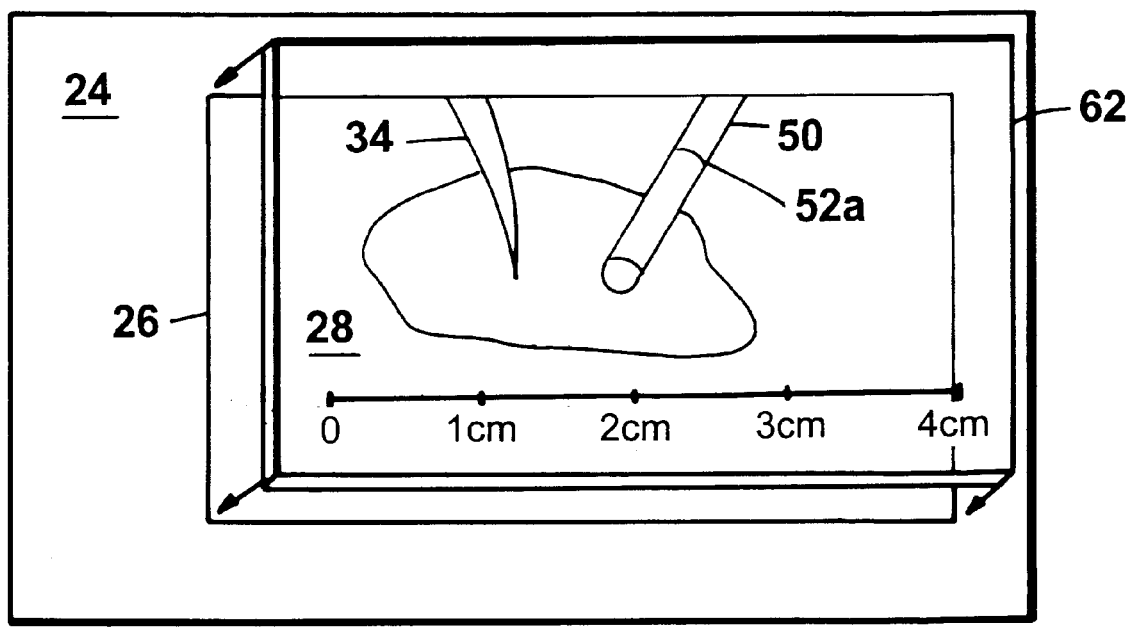

In other embodiments, a hardcopy measurement grid is prepared for each size factor. In this case, image processor 24 displays the image on monitor 26. Then, a member of the surgical team determines which of the visible graduations is closest to lens 22 and overlies the hardcopy measurement grid 62 for the size factor indicated by that graduation on monitor 26, as shown in FIG. 2b. The hardcopy measurement grid indicates a grid spacing in the image corresponding to a specific absolute dimension for the object being imaged. Each hardcopy measurement grid is a transparent sheet made from, e.g., plastic, having a grid formed or marked thereon.

Alternatively, there can be a single electronic or hardcopy measurement grid that measures the features of image 28 in some arbitrary unit, e.g., the actual size of the image as it appears on the display, and the size factor indicated by the probe provides a conversion factor that multiples a measure in the arbitrary units to give a measure in absolute units for the object. Depending on the embodiment, the conversion factors can be stored in image processor 24 or on some hardcopy chart. For example, the image processor may identify which of the visible graduations of measurement probe 50 is closest to lens 22, recall the conversion factor corresponding to that visible graduation, and display that conversion factor with the image, e.g., displaying a conversion factor of 1000 indicates that the actual size of the objects being viewed are one thousand times smaller than they appear on monitor 26.

Graduations and Size Factors

The magnification of endoscope 10 is calibrated to determine the size factors indicated by each of graduations 52. In many cases, the magnification M of the endoscope will smoothly decrease with the distance D between lens 22 and object 20. On the other hand, the size factor corresponding to a particular graduation is used for images produced by the endoscope over a range of distances and corresponding magnifications. Thus, since probe 50 measures the distance D with only a finite number of graduations, there is an error range associated with each of the size factors indicated by graduations 52. In general, the number of graduations should be sufficient to indicate the absolute size of features in image 28 to within an acceptable error.

In one embodiment, graduations 52 are spaced on probe 50 such that the fractional error in the measured size of features in image 28 are less than some constant value C. Fractional error is the error in the measure of a feature divided by the size of the feature. For example, for a polyp having a diameter of =mm and the measurement error is +/−0.5 mm, the fractional error is +/−0.1, or +/−10 percent.

To determine the correct spacings and corresponding size factors for the graduations, the magnification of the endoscope is calibrated empirically in a non-surgical procedure. To carry out the calibration, endoscope 10 produces images of a test pattern having known size dimensions over a range of distances D between lens 22 and the test pattern. The images are displayed on monitor 26, or alternatively, the images are recorded as photographs. The size of features of the images are compared to the known size of features of the test pattern to determine the exact magnification M of the endoscope for each of the distances D.

The distance D for each image is measured by extending probe 50 to contact the target tissue and measuring, e.g., using a ruler with very fine graduations, the length of probe visible in the image. This distance, which is called the apparent distance D', is somewhat different from the actual distance D between lens 22 and the test target. This is because the probe extends at a small angle to the optical axis of the lens 22 and because lens 22 cannot visualize probe 50 immediately after it exits the endoscope. Probe 50 must extend a short distance from the endoscope before it is in the field of view of lens 22. Thus, the apparent distance D' is typically smaller than the actual distance D. However, since the apparent distance D' is easily determined from an image including probe 50, it is preferred that the calibration be based on the apparent distance D', and not the actual distance D.

From the calibration measurements, there are a number of ways to determine a correct set of size factors and graduation spacings for a given constant fractional error C. For example, the size factors can be magnification factors or conversion factors, which are reciprocals of one another. Magnification factors multiply the actual size of an object to give the size of the object as it appears in image 28. Conversion factors multiply the size of an object as it appears in image 28 to give the actual size of the object. In one embodiment, a best-fit function f for the magnification M in terms of the apparent distance D' is determined from the calibration measurements, i.e., M=f(D').

Figure 3:
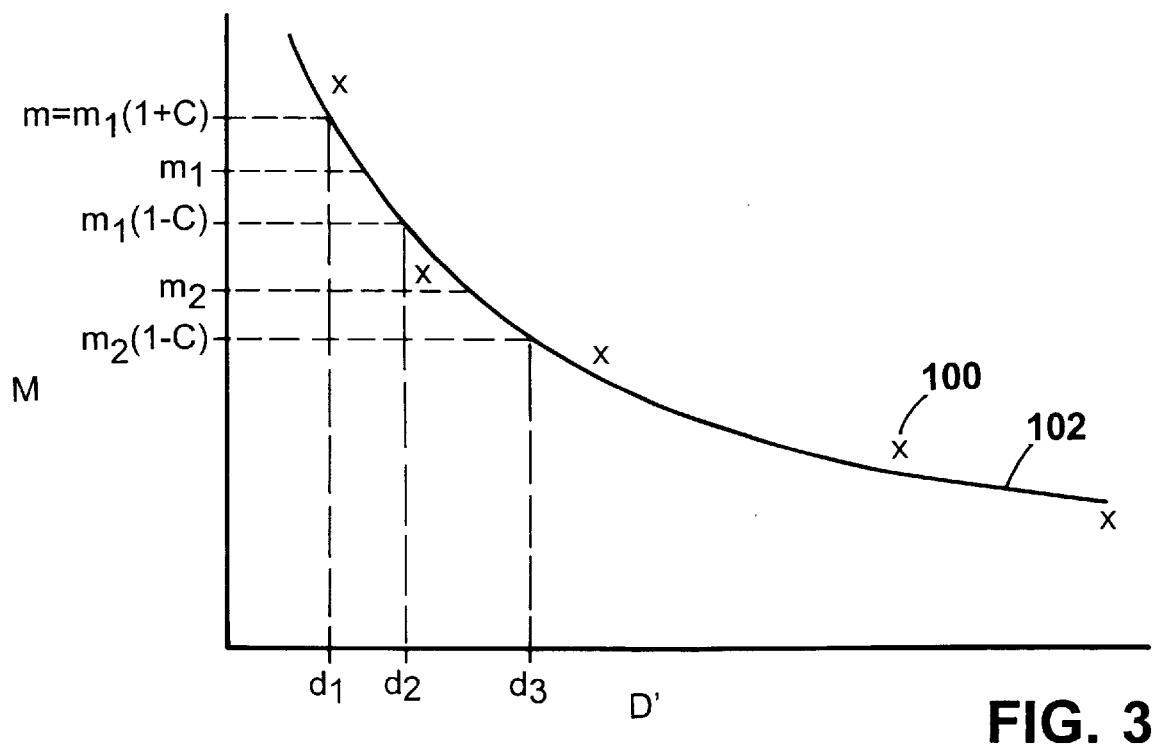
FIG. 3 is a graph of magnification M by the endoscope in FIG. 1 versus apparent distance D' as measured by the measurement probe in FIG. 1.

For example, for the set of data points 100 shown in FIG. 3, a best fit line 102 is drawn through the data points. As shown, f(D') is typically a smoothly decreasing function for most endoscopes, which are single lens systems. From the best fit line, one determines the magnification m=f($d_1$) corresponding to the magnification for an apparent distance where only the very tip of probe 50 is visible, i.e., d1 is approximately equal to zero. Then, the magnification factor m1 for the first graduation is given by $m_1$=m/(1+C), where the first graduation is given by D'=$d_1$. The location of the second graduation is given by the apparent distance $d_2$ such that f($d_2$)=$m_1$*(1−C). Thus, as shown in FIG. 3, whenever only the first graduation is visible, the actual magnification M(D') is within the constant fractional error C of the magnification factor $m_1$, i.e., if $d_1$<D'<$d_2$ then $m_1$*(1+C)>M(D')>$m_1$*(1−C). As described in greater detail below, one can refer to the apparent distances between the first graduation (the probe tip) and the second graduation as the first band. Thus, for any apparent distance in the first band the size factor $m_1$ gives the correct magnification to within the constant fractional error C.

The magnification factors and locations for subsequent graduations can be determined iteratively. For example, referring again to FIG. 3, the magnification factor for the second graduation is $m_2$=$m_1$*(1−C)/(1+C) and the location of the third graduation is given by $d_3$ such that f($d_3$)=$m_2$*(1−C). Thus, for apparent distances D' in the second band, i.e., $d_2$<D'<$d_3$, the magnification M is within a constant fractional error C of the second magnification factor $m_2$, i.e., if $d_2$<D'<$d_3$ then $m_2$*(1+C)>M(D')>$m_2$*(1−C). Continuing the iteration, for the nth band, i.e., $d_n$<D'<$d_{n+1}$, the location of the nth+1 graduation and the nth size factor satisfy:

$$m_n = m_{n-1} * [(1-C)/(1+C)] \quad (1)$$
$$= [m/(1-C)] * [(1-C)/(1+C)]^n$$

$$f(d_{n+1}) = m_n * (1-C) \quad (2)$$

The magnification factors determined using the above method provide an accurate magnification (to within the fractional error C) for features that appear in image 26. Such size factors are useful for the embodiments shown in FIGS. 2a and 2b where the size factor is used to generate a measurement grid spaced in units corresponding to the actual size of the objects being viewed. For example, for a magnification factor of 6 and a measurement grid that measures the actual size of objects being viewed in units of 5 mm, the measurement grid spacings would by 3 cm.

Alternatively, for a measurement grid that measures the size of objects as they appear in the image, one uses size factors that are conversion factors. In this case the conversion factor multiples the size of an object as it appears in the image to the actual size of the object. For example, for a conversion factor of ⅙, and a measurement grid that measures the size of an object as it appears in image to be 3 cm, the actual size of the object would be 5 mm.

Conversion factors gn can be determined by taking the reciprocal of the magnification size factor mn determined in the calibration above, i.e., $g_n=1/mn$. Alternatively, in some embodiments, the calibration is carried out in terms of conversion factors rather than magnification.

In such cases, one first determines data points for magnification M as a function of apparent distance D', as before. Thereafter, rather than determining a best fit line for M=f (D'), one determines a best fit line for G=h(D'), where G is defined as the inverse of M, i.e., G=1/M. Then, one determines the conversion factor $g=h(d_1)$ corresponding to an apparent distance $d_1$ where only the very tip of probe 50 is visible, i.e., $d_1$ is approximately equal to zero. Then, the conversion factor $g_1$ for the first graduation is given by $g_1=g/(1-C)$, where the first graduation is at the location $D'=d_1$. The location of the second graduation is given by the apparent distance $D'=d_2$ such that $h(d_2)=g_1*(1+C)$. Continuing as before requires that conversion factors $g_n$ and graduation locations $d_n$ satisfy:

$$g_n = g_{n-1} * [(1+C)/(1-C)] \quad (3)$$

$$= [g/(1+C)] * [(1+C)/(1-C)]^n$$

$$h(d_{n+1}) = g_n*(1+C) \quad (4)$$

In some cases, the best fit line for G is linear, i.e., G=h(D')=(a*D')+b. In such cases, there is the following expression for the graduation spacing:

$$d_{n+1}d_n = 2*C*g_n/a \quad (5)$$

Also, the locations of the graduations can be expressed as:

$$d_n = (1/a) * \{g*[(1+C)/(1-C)]^{n-1} - b\} \quad (6)$$

Colored Bands

Figure 4:
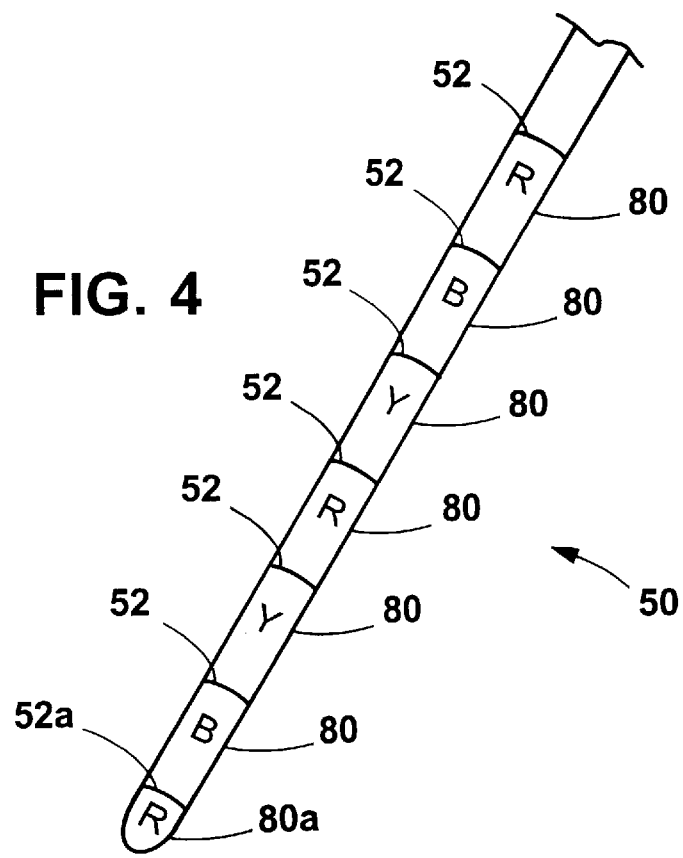
FIG. 4 is a schematic diagram of an embodiment for the measurement probe in FIG. 1.

FIG. 4 shows a schematic of an embodiment for probe 50. Graduations 52 are defined by the boundary between adjacent bands 80. If the tip of probe 50 is referred to as the first graduation, the portion of the probe between the tip and the second graduation 52a is the first band 80a. Unevenly spaced graduations 52 correspond to bands having unequal widths. To more easily distinguish between graduations and/or bands, the bands are colored as shown in FIG. 4, R for red, B for blue, and Y for yellow.

In some embodiments, every band has a different color. Thus, when using the endoscope, image processor 24 or a member of the surgical team, identifies the color of the visible band nearest the endoscope in image 28 and selects the size factor corresponding to that band. In many cases, identifying such a color is easier than counting the number of graduations or bands between the tip of probe 50 and the visible portion of the probe nearest the endoscope in image 28.

In other embodiments, at least one pair of bands have the same color, but the sequence of colors on probe 50 are such that the colors of the two bands nearest the endoscope in image 26 uniquely specifies a particular size factor. For example, in FIG. 4 the color of the bands from the tip of probe 50 is red, blue, yellow, red, yellow, blue, and red.

Thus, the colors of the two bands nearest the endoscope in the image and their order uniquely specify the band and its corresponding size factor, as shown below:

TABLE 1

| Band | Order Color Pair |
|------|------------------|
| 1 | red |
| 2 | red, blue |
| 3 | blue, yellow |
| 4 | yellow, red |
| 5 | red, yellow |
| 6 | yellow, blue |
| 7 | blue, red |

Types of Endoscopes

The measurement probe can be used with a wide variety of endoscopes, including colonoscopes, laparoscopes, arthroscopes, gastroscopes, and laryngoscopes. Also the endoscope can be flexible or rigid, and can utilize an optical fiber or a charged coupled device (CCD) camera. Furthermore, rather then being passed through an instrument channel, in other embodiments the probe can be connected to the endoscope and extended telescopically to contact the object being viewed.

EXAMPLE

A commonly used colonoscope (Olympus Model 1T100L) was used to obtain images of a test target for various endoscope-target apparent distances. As described above, apparent distance D' is defined as the distance between the first visible band on the probe and the tip of the probe. For this instrument, the actual distance from the target to the end of the endoscope is approximately 7 mm greater than the apparent distance.

Figure 5:
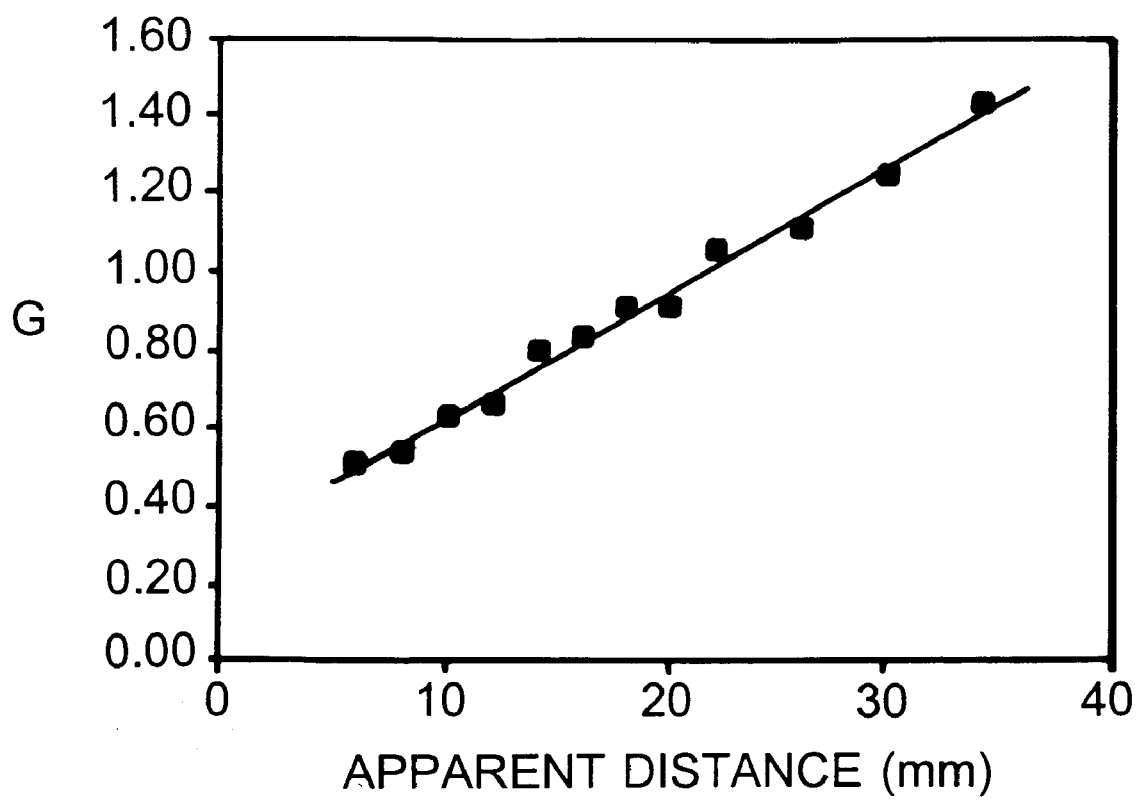
FIG. 5 is a graph of conversion values G versus apparent distance D' for a calibration of the measurement probe.

The magnification M was determined by measuring the apparent size of the test pattern as it appeared on printed photos of the endoscopic image and dividing it by the actual size. The magnification M values were then converted to conversion values G, where G=1/M. The values for G were then plotted as a function of apparent distance D' and fit to a line using a linear regression, i.e., G=(a*D')+b, as shown in FIG. 5. For the Olympus instrument under study, the linear regression analysis demonstrated that G was a linear function of x(r=0.99) with best fit parameters of a=0.033 and b=0.30. Under these conditions, the fractional error C, which equals the error in G divided by G, can be related to a corresponding error X in apparent distance D' as follows:

$$X = [(a*D')+b]*C/a \quad (7)$$

Eq. 7 implies that the exact conversion value g for the apparent distance d, i.e., G(d)=g, is accurate to within the fractional error C for apparent distances within X of d. Or, in other words, if d−X<D'<d+X, then 1−C<G(D')/g<1+C. Eq. 7 is similar to eq. 5 with $X=(d_{+1}-d_n)/2$.

Using the regression analysis values for the Olympus instrument and Eq. 7 for a fractional error C equal to 0.1 or 10%, the following holds:

TABLE 2

| Apparent Distance D' (mm) | Corresponding Error X (mm) |
|---------------------------|----------------------------|
| 5 | 1.4 |
| 10 | 1.9 |
| 15 | 2.4 |

TABLE 2-continued

| Apparent Distance D' (mm) | Corresponding Error X (mm) |
|---|---|
| 20 | 2.9 |
| 25 | 3.4 |
| 30 | 3.9 |

The information in Table 2 was then used to construct a probe with graduations adjusted to provide conversion factors G to within a 10% error. This prototype probe had the sequence of colored bands shown in Table 3 below.

TABLE 3

| Apparent Distance D' (mm) | Band Length (mm) | Band Color |
|---|---|---|
| 5.0 | 1.5 | Black |
| 6.5 | 1.5 | White |
| 8.0 | 1.7 | Red |
| 9.7 | 1.8 | White |
| 11.5 | 2.1 | Green |
| 13.6 | 2.3 | White |
| 15.9 | 2.5 | Blue |
| 18.4 | 2.8 | White |
| 21.2 | 3.1 | Yellow |
| 24.3 | 3.4 | White |
| 27.7 | 3.8 | Black |

To test the probe, endoscopic photos of a dime (18 mm indicator) were taken for a number of different apparent distances. The calibration and test measurements were performed using two different endoscopes of the same model. To determine the size of the dime, the dime was imaged with the probe in view and the photo was taken. The color coding of the probe indicated the apparent distance to the target and the conversion factor G was computed using the calibration data or the regression results, i.e., G=(a*D')+b. The conversion factor was then use to multiply the size of the dime as it appeared in the photo to estimate the actual size of the dime. The results are shown below in Table 4. The error in Table 4 is defined as the difference between the actual size (18 mm) and the corrected size divided by the actual size and expressed in percent.

TABLE 4

| Band Color | Apparent Distance (mm) | Size on Photo (mm) | G | Corrected Size (mm) | % Error |
|---|---|---|---|---|---|
| Green | 13 | 26 | 0.71 | 18.5 | −3 |
| Red | 9 | 28 | 0.59 | 16.5 | 8 |
| Yellow | 23 | 18 | 1.04 | 18.7 | −4 |
| Blue | 17 | 21 | 0.86 | 18.1 | 0 |
| Red-White | 11 | 27 | 0.64 | 17.3 | 4 |

As desired, the errors were within the catheter design accuracy of 10%. The mean error of these measurements was 4% using working distances ranging between 14 and 30 mm (apparent distance range 9–23 mm).

Other Embodiments

It is to be understood that while the invention has been described in conjunction with the detailed description thereof, that the foregoing description is intended to illustrate and not limit the scope of the invention, which is defined by the scope of the appended claims. For example, in other embodiments the graduations of the probe may be spaced so that the size of an object as it appears in an image scaled by the appropriate size factor is always within a constant absolute error of the object's actual size. Calibration for such a probe could be performed in a manner similar to that described with reference to FIG. 3, except that bands for magnification M would be defined in terms of constant absolute error rather than constant fractional error.

Other aspects, advantages, and modifications are within the scope of the following claims.

What is claimed is:

1. An endoscopic imaging system for viewing an object within a patient's body cavity, the system comprising:
    an endoscope for viewing an image of the object, the endoscope comprising a distal end, an instrument channel extending therethrough, and a lens at the distal end adjacent the instrument channel; and
    an elongate probe configured to be inserted through the instrument channel and contact the object, the probe comprising a plurality of unevenly spaced graduations along its length, each graduation indicating a size factor used to scale the image produced by the endoscope.

2. The system of claim 1, wherein the graduations on the probe are spaced such that an image of the object scaled by the size factor corresponding to the graduation nearest the distal end of the endoscope in the image is of a size that is within a constant error of an actual size of the object.

3. The system of claim 2, wherein the constant error is about 10 percent.

4. The system of claim 1, wherein the spacing between each pair of adjacent graduations s(N) is substantially equal to an equation given by:

$$s(N)=w*y^N$$

where w and y are constants, and N is the number of graduations between the pair and a distal end of the probe.

5. The system of claim 1, wherein the plurality of graduations are defined by a plurality of bands extending along the length of the probe.

6. The system of claim 5, wherein at least two of the plurality of bands each have a different color.

7. The system of claim 5, wherein the plurality of bands each have a different color.

8. The system of claim 6, wherein the colors of an adjacent pair of bands indicate a unique graduation.

9. The system of claim 1, wherein the endoscope has an additional instrument channel.

10. The system of claim 1, further comprising an analyzer storing the size factors, wherein the analyzer is programmed to receive the image from the endoscope, identify which of the graduations visible in the image is nearest the distal end of the endoscope, and specify the size factor corresponding to the identified graduation.

11. The system of claim 10, further comprising a monitor connected to the analyzer, wherein the monitor displays the image viewed through the endoscope and overlays the image with an electronic measurement grid corresponding to the specified size factor.

12. The system of claim 1, further comprising a monitor connected to the endoscope for displaying the image.

13. The system of claim 12, further comprising a series of measurement grids configured to overlay the image displayed on the monitor, wherein each measurement grid corresponds to one of the size factors indicated by the graduations of the probe.

14. An endoscopic imaging system for viewing an object within a patient's body cavity, the system comprising:
    an endoscope for viewing an image of the object, the endoscope comprising a distal end and a lens at the distal end; and an elongate probe connected to the endoscope and extendable to contact the object, the probe comprising a plurality of unevenly spaced graduations along its length, each graduation indicating a size factor used to scale the image viewed through the endoscope.

15. A method of determining the size of an object in a patient's body cavity, the method comprising:

generating an image of the object using an instrument;

extending a probe having a series of unevenly spaced graduations from the instrument to the object;

identifying the graduation on the probe visible in the image nearest to the instrument; and scaling the image viewed by the endoscope by a size factor corresponding to the identified graduation.

16. The method of claim 15, wherein scaling comprises overlaying the image viewed through the instrument with a measurement grid corresponding to the size factor.

17. The method of claim 15, wherein the instrument is an endoscope.

18. A probe for determining a size of an object viewed through an endoscope, the probe comprising:

an elongate shaft configured for use with the endoscope and to contact the object; and a plurality of unevenly spaced graduations located along a length of the shaft, each graduation indicating a size factor used to scale the size of the object viewed through the endoscope.

19. The probe of claim 18, wherein the shaft is configured to be inserted through an instrument channel of the endoscope.

20. The probe of claim 18, wherein the graduations on the probe are spaced such that an image of the object scaled by the size factor corresponding to the graduation nearest the distal end of the endoscope in the image is of a size that is within a constant error of an actual size of the object.

21. The probe of claim 20, wherein the constant error is about 10 percent.

22. The probe of claim 18, wherein the spacing between each pair of adjacent graduations s(N) is substantially equal to an equation given by:

$$s(N) = w * y^N$$

where w and y are constants, and N is the number of graduations between the pair and a distal end of the probe.

23. The probe of claim 18, wherein the plurality of graduations are defined by a plurality of bands extending along the length of the probe.

24. The probe of claim 18, wherein at least two of the plurality of bands each have a different color.

* * * * *